United States Patent
West

(10) Patent No.: US 6,403,811 B1
(45) Date of Patent: Jun. 11, 2002

(54) RECOVERY OF CHROMAN DERIVATIVES

(75) Inventor: Simon Michael West, Williamstown (AU)

(73) Assignee: Swig Pty Ltd, Malvern Victoria (AU)

( * ) Notice: Subject to any disclaimer, the term of this patent is extended or adjusted under 35 U.S.C. 154(b) by 0 days.

(21) Appl. No.: 09/890,057

(22) PCT Filed: Jan. 25, 2000

(86) PCT No.: PCT/AU00/00038

§ 371 (c)(1),
(2), (4) Date: Jul. 25, 2001

(87) PCT Pub. No.: WO00/43380

PCT Pub. Date: Jul. 27, 2000

(30) Foreign Application Priority Data

Jan. 25, 1999 (AU) .................................................. 8293

(51) Int. Cl.[7] ............................................. C07D 311/72
(52) U.S. Cl. .......................... 549/220; 549/201; 549/413
(58) Field of Search ................................ 549/201, 220, 549/413

(56) References Cited

U.S. PATENT DOCUMENTS 3,212,901 A * 10/1965 Robeson ..................... 514/458

FOREIGN PATENT DOCUMENTS

| EP | 0 171 009 A2 | 2/1986 |
| EP | 0 338 429 A2 | 10/1989 |
| WO | 0 641 790 A1 | 3/1995 |
| WO | WO 00/69865 | 11/2000 |

OTHER PUBLICATIONS

Xiandai Huagong, (1987), 17(7), Lei, Bingfu and Sun, Dengwen "Progress in alpha–tocopherol preparation technology", & Chemical Abstracts #129:113349. See whole abstract.

Arq.Biol.Technol. (1994), 37(4) , 1003–1011, Almeida, Mem et .al., "Evaluation of soybean oil deodorization distillate for Vitamin E recovery", & Chemical Abstracts #123:142172. See Whole document.

Biosci.Biotechnol.Biochem., 62(12), 2463–2466, 1998, Miyamoto, S. et al., "Synthesis of a Novel Phosphate Ester of a Vitamin E Derivative and Its Antioxidative Activity", & Medline Abstract #1999138223. See abstract and p. 2463 column 1, line 12.

JP 53015381 (EISAI Co. Ltd.) Feb. 13, 1978, & Patent Abstracts of Japan #10045783. See whole abstract.

JP 10045783 (Showa Denko KK) Feb. 17, 1998, & Patent Abstracts of Japan #10045783. see whole abstract.

* cited by examiner

Primary Examiner—Fiona T. Powers
(74) Attorney, Agent, or Firm—Michael Best & Friedrich LLP; Grady J. Frenchick

(57) ABSTRACT

A process for recovering a concentrate of chromans from a distillate containing chromans is provided comprising the steps of: (1) forming chroman phosphates in the distillate; (2) subjecting the distillate to shearing forces, in the presence of a gas of flotation to form a froth; and (3) recovering the froth containing the concentrate of chroman phosphates.

18 Claims, No Drawings

RECOVERY OF CHROMAN DERIVATIVES

FIELD OF THE INVENTION

The invention relates to a method of recovering a concentrate of chromans from a mixture containing chromans.

BACKGROUND TO THE INVENTION

The chromans are a commercially valuable group of chemicals that show biological activity as vitamin E and antioxidant properties. In this specification and the claims, the term "chromans" includes chroman and derivatives of chroman such as the hydroxy chromans tocopherol and tocotrienol (commonly referred to as the "tocols"), the alpha, beta gamma and delta forms corresponding to 3,2,1 and 0 methyl groups. They are often used as dietary supplements. Chromans are second tier free radical scavengers in animals and humans which work with vitamin C and ubiquinone to minimize oxygen damage to cells.

Chromans are present in many natural lipids. Chroman concentrates are prepared from the "distillate" created while deodorising the lipids. Lipids are deodorised using a distillation process designed to remove volatile products. The volatile products are principally free fatty acids, but also include aldehydes from oxidation and many other substances. The molten lipid is either purged with super heated steam injection or spread on a large surface in a flowing steam flux. The volatiles (including the chromans) and the steam are then condensed and the non-aqueous fraction recovered as the "distillate".

Presently, the main source of vitamin E is RRR-α-tocopherol derived from soybean oil. The raw oil is stripped with steam to strip the lower molecular weight free fatty acid ("FFA") from the oil which has a molecular weight three times that of the FFA. The chromans have a similar molecular weight to the FFA and therefore follow the FFA into the distillate. The distillate is then redistilled to give a higher concentration of chromans. Typically, the chromans must then be methylated to give vitamin E.

There are two main problems with the known process. First, if there is a low concentration of chromans, the relative vapour pressure between the chromans and the FFA in the distillate is insufficient to enable satisfactory concentration. Second, during the distillation a high concentration of tocotrienols, phytol and farnesene form and these compounds have a low vitamin E activity. Further, the process based on a series of distillations is inefficient and uses a lot of energy and capital plant.

As a result, investigations were made into developing a process to concentrate chromans which avoids the high temperature refining process.

There is a well known art for concentrating hydrophobic molecules from high surface tension bulk liquids such as water by using froth flotation. However, this art is not applicable to "distillates" which are mainly $C_{18}$–$C_{22}$ FFA, because detergents suitable for aqueous systems do not stabilise a froth of FFA. The chromans present in the distillate do not significantly accumulate on the air/fatty acid interface as both molecules have similar surface properties in the FFA phase.

Therefore, further investigations were made into the possible use of froth concentration to achieve a chroman concentrate.

DESCRIPTION OF THE INVENTION

It was found that the chromans can be concentrated by froth flotation if the chromans were activated by phosphorylation. The phosphorylated chromans are insoluble in the FFA and form a brittle froth that contains a higher concentration of chromans than the FFA phase.

Accordingly, a process of recovering a concentrate of chromans from a distillate containing chromans is provided comprising the steps of:

(1) forming chroman phosphates in the distillate;

(2) subjecting the distillate containing chroman phosphates to shearing forces, in the presence of a gas of flotation to form a froth; and (3) recovering the froth containing the concentrate of chroman phosphates.

In one preferred form, the froth could be further stabilised by additions of small quantities of silicone surfactant and water. Preferably, the silicone surfactant concentration is between 0.01 to 0.0001%.

The froth could also be further stabilized by the addition of a sugar such as glucose. The sugar is added to complex with the chroman phosphates and would typically be present in a mole ratio to the chromans of 0:1 to 2:1. The froth can also be stabilized by forming a chroman phosphate salt with sodium or potassium.

Any convenient method of phosphorylation can be used to form the chroman phosphates. Typically, the phosphorylation is performed by addition of excess of poly phosphoric acid (eg about 50% mole excess), with strong stirring to generate an emulsion in the molten fatty acid. The phosphorylation reaction may be further enhanced by the addition of a soap such as sodium oleate (eg three moles of soap relative to the poly phosphoric acid), then by allowing the reaction to proceed for 15 to 45 minutes (preferably about 30 minutes). The addition of a soap increases the solution concentration of the reagent.

Preferably, the chromans are phosphorylated using $P_4O_{10}$ as per the method disclosed in Australian provisional patent application PQ0374 (International Publication Number WO 00/69865) at a temperature at which the FFA is liquid. The contents of Australian provisional patent application PQ0374 (International Publication Number WO 00/69865) are hereby incorporated by reference. The $P_4O_{10}$ is used in equal mole ratio to chromans. Typically, the amount of chromans is 1% of distillate.

Preferably, the temperature at which the process is carried out varies from the melting point of the "distillate" to about 200° C.

The gas of flotation used in the process is preferably air, but other gases inert to the process may be used. For example carbon dioxide or nitrogen gas would be suitable as gases with limited solubility but yet capable of generating bubbles where there is a finite surface tension at the gas/liquid interface.

Preferably, the shearing forces are applied using an aerator. The aerator must be capable of generating a stream of bubbles of no more than 3 mm diameter. In this respect, the aerator will give shear sufficient to intimately mix the distillate with the chemical additives. Standard aerators used for froth flotation are not suitable for viscous material.

EXAMPLES

The invention will now be further illustrated by the following non-limiting examples.

Example 1

A flotation vessel was formed as a cylinder of diameter 50 mm and height 300 mm with a lipped port 40 mm from the top as the froth exit. The vessel was filled to 30 mm below the port with molten distillate, then a high shear stirrer and gas line inserted to the bottom. 4 g of polyphosphoric acid were added slowly with stirring, then 8 g of sodium oleate soap, whilst maintaining the temperature at about 70° C. After 30 minutes stirring air was introduced near the stirrer to generate a fine stream of bubbles. A froth formed which was stabilised to allow bubbles to pass over the lipped port by careful addition of silicone oil and three drops of water. The froth was recovered and analysed to find 0.67% tocopherol whilst 0.16% tocopherol was found in the bulk phase.

Example 2

A flotation cell was configured as an octagonal vertical vessel with a tapered bottom and glass lined.

The vessel was partially filled with palm oil fatty acid distillate (293 kg) and brought to 75° C. by using hot water in the jacket of the vessel. Once the distillate was at 75° C., the volume was corrected to be 50 mm below the top lip of the vessel.

A pump was used to pump the molten distillate through the aerator device and back into the vessel to discharge 250 mm below the liquid surface.

$P_4O_{10}$ (870 g) was added over 3 minutes using the agitation of the circulating pump, and a conditioning period of 5 minutes was allowed for reaction. The air supply to the aerator was slowly increased and Silwet L-7622 (a silicone surfactant) (6 g) and water (230 g) added slowly to give a froth that was sufficiently stable to pass across the lip of the vessel into a launder.

The initial concentration of alpha tocotrienol was 0.71%. The froth was collected to give 9.8 kg of concentrate that contained 5.1% of alpha tocotrienol and 0.41% of alpha tocopherol.

The word 'comprising' and forms of the word 'comprising' as used in this description does not limit the invention to exclude any variants or additions.

Modifications and improvements to the invention will be readily apparent to those skilled in the art. Such modifications and improvements are intended to be within the scope of this invention.

The claims defining the invention are as follows:

1. A process of recovering a concentrate of chromans from a distillate containing chromans comprising the steps of:
   (a) forming chroman phosphates in the distillate;
   (b) subjecting the distillate containing chroman phosphates to shearing forces, in the presence of a gas of flotation to form a froth; and
   (c) recovering the froth containing the concentrate of chroman phosphates.

2. A process according to claim 1 wherein the froth is stabilized by addition of silicone surfactant and water.

3. A process according to claim 2 wherein the silicon surfactant concentration is between 0.01–0.0001%.

4. A process according to claim 1 wherein the froth is stabilised by addition of sugars.

5. A process according to claim 4 wherein the sugar is glucose.

6. A process according to claim 5 wherein the glucose to chroman mole ratio is up to 2:1.

7. A process according to claim 1 wherein the chromans are phosphorylated using polyphosphoric acid.

8. A process according to claim 1 wherein the chromans are phosphorylated using $P_4O_{10}$.

9. A process according to claim 1 wherein the temperature at which the process occurs is in the range from the melting point of the distillate to 200° C.

10. A process according to claim 9 wherein the process occurs at a temperature in the range from 70° C. to 100° C.

11. A process according to claim 1 wherein the gas of flotation is selected from air, carbon dioxide, nitrogen or other inert gases.

12. A process according to claim 11 wherein the gas of flotation is air.

13. A process according to claim 1 wherein the shearing forces are applied using an aerator.

14. A process of recovering a concentrate of chromans from a distillate containing chromans comprising the steps of:
   (a) forming chroman phosphates in the distillate;
   (b) subjecting the distillate containing chroman phosphates to shearing forces, in the presence of a gas of flotation and a stabilizer selected from the group consisting of silicone surfactants, sugars and mixtures thereof to form a froth; and
   (c) recovering the froth containing the concentrate of chroman phosphates.

15. A process of recovering a concentrate of chromans from a distillate containing chromans comprising the steps of:
   (a) forming sodium or potassium chroman phosphate salts in the distillate;
   (b) subjecting the distillate containing chroman phosphates to shearing forces, in the presence of a gas of flotation to form a froth; and
   (c) recovering the froth containing the concentrate of chroman phosphates.

16. A process of recovering a concentrate of chromans from a distillate containing chromans comprising the steps of:
   (a) forming chroman phosphates in the distillate using a phosphorylating agent selected from the group consisting of polyphosphoric acid and $P_4O_{10}$;
   (b) subjecting the distillate containing chroman phosphates to shearing forces, in the presence of a gas of flotation to form a froth; and
   (c) recovering the froth containing the concentrate of chroman phosphates.

17. A process of recovering a concentrate of chromans from a distillate containing chromans comprising the steps of:
   (a) forming chroman phosphates in the distillate at a temperature in the range of from 70° to 100° C.;
   (b) subjecting the distillate containing chroman phosphates to shearing forces, in the presence of a gas of flotation to form a froth; and
   (c) recovering the froth containing the concentrate of chroman phosphates.

18. A process of recovering a concentrate of tocopherols and tocotrienols from a distillate comprising the steps of:
   (a) forming tocopheryl phosphates and tocotrienol phosphates in the distillate;
   (b) subjecting the distillate containing tocopheryl phosphates and tocotrienol phosphates to shearing forces, in the presence of a gas of flotation to form a froth; and
   (c) recovering the froth containing the concentrate of tocopheryl phosphates and tocotrienol phosphates.

* * * * *